United States Patent
Andrew et al.

(10) Patent No.: US 8,137,981 B2
(45) Date of Patent: Mar. 20, 2012

(54) APPARATUS AND ASSOCIATED METHODS

(75) Inventors: Piers Andrew, Cambridge (GB); Jani Kivioja, Cambridgeshire (GB); Hongwei Li, Cambridge (GB); Marc Bailey, Cambridge (GB); Richard White, Huntingdon (GB)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 12/698,958

(22) Filed: Feb. 2, 2010

(65) Prior Publication Data

US 2011/0189783 A1    Aug. 4, 2011

(51) Int. Cl.
*G01N 27/00* (2006.01)

(52) U.S. Cl. ............... 436/165; 436/164; 250/505.1; 356/445

(58) Field of Classification Search .......... 436/165, 436/164; 356/445; 250/505.1
See application file for complete search history.

(56) References Cited

U.S. PATENT DOCUMENTS

| 7,129,096 B2 | 10/2006 | Chilkoti |
| 7,319,046 B2 | 1/2008 | Misiakos et al. |
| 2005/0003520 A1* | 1/2005 | Misiakos et al. ........... 435/287.2 |
| 2005/0253137 A1* | 11/2005 | Whang et al. ............... 257/40 |
| 2007/0140638 A1 | 6/2007 | Yang |
| 2007/0252983 A1* | 11/2007 | Tong et al. .................. 356/301 |
| 2008/0080816 A1 | 4/2008 | D'Urso |

FOREIGN PATENT DOCUMENTS

| WO | WO2011014175 A1 | 2/2011 |
| WO | WO2011014176 A1 | 2/2011 |

OTHER PUBLICATIONS

E Lai et al, "Vertical Nanowire Array-Based Light Emitting Diodes", Nano Res. 1, 123 (2008).

J. Anker et al, "Biosensing with plasmonic nanosensors", Nature Materials, 7,442 (2008).
J. Johnson et al, "Optical Cavity Effects in ZnO Nanowire Lasers and Waveguides", J. Phys. Chem. B, 107, 8816 (2003).
J. Love et al, "Self-Assembled Monolayers of Thiolates on Metals as a Form of Nanotechnology", Chem. Rev. 105, 1103 (2005).
K. Willets et al, "Localized Surface Plasmon Resonance Spectroscopy and Sensing", Annu. Rev. Phys. Chem. 58,267 (2007).
M. Stewart et al, "Nanostructured Plasmonic Sensors", Chem. Rev. 108, 494 (2008).
N. Nath et al, "A Colorimetric Gold Nanoparticle Sensor to Interrogate Biomolecular Interactions in Real Time on a Surface", Anal. Chem. 74, 504 (2002).
T. Klar et al, "Nanophotonics with Surface Plasmons", Elsevier (Amsterdam) 2008, Chapter 8 "Biosensing with nanoparticles".
T. Okamoto et al, "Local plasmon sensor with gold colloid monolayers deposited upon glass substrates", Optics Letters, 25, No. 6, 372 (2000).
T. Voss et al, "High-Order Waveguide Modes in ZnO Nanowires", Nano Letters, 7, No. 12, 3675 (2007).
W. Park et al, "Electroluminescence in n-ZnO Nanorod Arrays Vertically Grown on p-GaN", Adv. Mater. 16, No. 1, 87 (2004).
Law et al., "Chemical sensing with nanowires using electrical and optical detection", Int. J. Nanotechnol., vol. 4, No. 3, pp. 252-261, 2007.
Malcolm, N.P. et al., "Simulation of a plasmonic tip-terminated scanning nanowire waveguide for molecular imaging", Applied Physics Letters, vol. 93, pp. 193101-1-193101-3, 2008.
ISR and Written Opinion of the International Searching Authority for PCT Application No. PCT/FI2011/050076, dated May 11, 2011.

* cited by examiner

*Primary Examiner* — Christine T Mui (74) *Attorney, Agent, or Firm* — Harrington & Smith (57) ABSTRACT

An apparatus comprising a nanowire waveguide with first and second ends, the second end comprising a nanoparticle, the nanowire waveguide configured to transmit radiation from the first end to the second end to illuminate the nanoparticle, the apparatus configured such that the nanoparticle is capable of being in close proximity to an analyte to allow for detection of said analyte.

21 Claims, 7 Drawing Sheets

APPARATUS AND ASSOCIATED METHODS

TECHNICAL FIELD

The present disclosure relates to the field of nanoscale optoelectronic sensors, associated methods and apparatus, and in particular concerns the integration of a light source with a nanowire waveguide and nanoparticle. One or more techniques described herein may or may not be suitable for the detection of impurities in battery solutions, or for health monitoring using portable electronic devices.

BACKGROUND

Surface plasmon resonance (SPR) spectroscopy is a label-free sensing technology that can monitor the thermodynamics and kinetics of biological binding processes, and more generally, real-time changes in the local dielectric environment. It has the potential as a mobile analytical system for the rapid detection of food-borne or environmental pathogens and for health monitoring. The current commercialised SPR systems, however, require external light sources which are not integrated with the sensor. The necessity for external light sources inhibits miniaturisation and mobility of the sensor, and demands precise alignment of the illumination.

A planar, chip-based localised surface plasmon resonance (LSPR) biosensor has been developed wherein a monolayer of gold nanoparticles are immobilised on a glass surface and subsequently functionalised with a biological ligand. Biomolecular binding events are sensed when the functionalised glass coverslip is immersed in a solution containing the target analyte by measurement of a change in surface plasmon absorbance associated with the gold nanoparticles as a result of the change in local refractive index. This method employs an external light source and photodetector. Details of this biosensor can be found in the following publications: Analytical Chemistry, 74, No. 3, 504 (2002); Optics Letters, 25, No. 6, 372 (2000); and U.S. Pat. No. 7,129,096.

There have been various reports [e.g. see Nano Res 2008, 1: 123-128 and Adv. Mater., 16, No. 1, 87 (2004)] of electroluminescence devices employing n-type ZnO nanowires synthesised atop p-type GaN surfaces. Evidence suggests that the nanowires themselves act as waveguides to the light generated at the p-n junction. In the devices reported so far, there are contributions to the electroluminescence spectrum from band-band transitions, acceptor to band transitions in GaN, and defect states. Furthermore, these devices all employ metallic layer top contacts to the ZnO nanowires which are not transparent to the light generated and prevent further functionalisation of the nanowire tips.

US patent application no. US 2007/0140638 A1 describes the application of nanowires and nanoribbons which have diameters lower than the wavelength of light as optical waveguides for the formation of optical circuits and devices. The focus of this document is on the general application of nanowires as waveguides (specifically ZnO and SnO2 nanowires), the coupling of light between adjacent nanowires, and optical sensors based on a single nanowire waveguide integrated with multiple microfluidic channels.

U.S. Pat. No. 7,319,046 B2 describes an integrated optoelectronic silicon biosensor for the detection of biomolecules labelled with chromophore groups or nanoparticles. This biosensor comprises a p-n junction light-emitting diode (LED) light source and a p-n junction LED photodetector, and couples the light between them using a silicon nitride optical waveguide. The waveguide is integrated with a microfluidic channel and interfaces with the biological medium where modulation of the optical coupling takes place.

None of the prior art documents describe a nanoscale LSPR sensor comprising an integrated light source, waveguide and nanoparticle.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an apparatus comprising a nanowire waveguide with first and second ends, the second end comprising a nanoparticle, the nanowire waveguide configured to transmit radiation from the first end to the second end to illuminate the nanoparticle, the apparatus configured such that the nanoparticle is capable of being in close proximity to an analyte to allow for detection of said analyte. On the other hand, the apparatus may be configured to bind to an analyte to allow for detection of said analyte. The expression "close proximity" in this case may imply that the analyte is on or near the surface of the nanoparticle. When the analyte is "near" the surface of the nanoparticle, the distance between the nanoparticle and the analyte may be of the order of the nanoparticle dimensions or less. For example, the distance between the nanoparticle and the analyte may be less than or equal to the diameter of the nanoparticle. The expression "close proximity" may mean that the analyte is within the evanescent field of the nanoparticle's localised surface plasmon resonance (LSPR).

The apparatus may comprise a radiation source capable of emitting radiation. The first end of the nanowire waveguide may be attached to the radiation source to direct radiation generated by the radiation source to the second end of the nanowire waveguide. The apparatus may be configured such that the nanowire waveguide is attached end on to the radiation source to direct radiation generated by the radiation source to the free end of the nanowire waveguide. The radiation source may be a substrate capable of emitting radiation. The substrate may comprise a light-emitting diode. The substrate and nanowire waveguide may together form a p-n junction of a light-emitting diode.

The apparatus may comprise electrical contacts configured to enable a flow of charge carriers between the substrate and the nanowire waveguide. The electrical contacts may be configured to be physically isolated from the nanoparticle. The apparatus may comprise first and second electrical contacts. The first electrical contact may be configured to be in physical contact with the substrate and the second electrical contact may be configured to be in physical contact with the nanowire waveguide. The first and second electrical contacts may be configured to be physically isolated from one another. Advantageously, the second electrical contact may be configured to be physically isolated from the substrate and analyte by electrically insulating material. Also, the first electrical contact, the second electrical contact, and the insulating material may be configured to be transparent to the radiation generated by the substrate. The refractive index of the first electrical contact, the second electrical contact, and the insulating material may be configured such that total internal reflection of the radiation occurs within the nanowire waveguide.

The apparatus may comprise an array of nanowire waveguides. Some or all of the nanowire waveguides may have a nanoparticle attached to their respective free ends. The apparatus may comprise one or more nanowire waveguides. Some or all of the nanowire waveguides may have a diameter within a range of 50 and 300 nm or within a range of 100 and 300 nm.

The nanoparticle may be configured to be functionalised such that it is capable of binding to the analyte. The nanoparticle may be functionalised by the adsorption of a functionalisation molecule onto the surface of the nanoparticle. The apparatus may comprise electrical contacts configured to induce electrodesorption of the functionalised molecule at the surface of the nanoparticle.

The nanoparticle may be configured to be capable of supporting surface plasmons, and the radiation emitted by the substrate may be configured to be capable of exciting a localised surface plasmon resonance at the interface between the nanoparticle and the analyte.

The apparatus may be configured for use as a transmitter in spectroscopy. The apparatus may be configured for use as a transmitter in Surface Enhanced Raman Spectroscopy. The apparatus could, however, be a module configured for use in a transmitter in spectroscopy.

According to a further aspect, there is provided a sensor comprising a radiation detector and any apparatus described herein. The sensor may be configured for use in localised surface plasmon resonance spectroscopy. The apparatus may comprise more than one array of nanowire waveguides. Advantageously, the respective arrays may be configured to be spaced apart from one another on the substrate such that the sensor is able to perform multiplexed sensing measurements. The sensor may be integrated within a microfluidic system. The radiation detector may comprise a charge-coupled device camera and a spectrometer. The sensor may be configured such that the wavelength and intensity of the radiation emitted by the substrate, after illuminating the analyte, is detected by the radiation detector.

According to a further aspect, there is provided a method for producing an apparatus to allow for detection of an analyte, the method comprising:

providing a radiation-emitting substrate;
providing a nanoparticle on the surface of the radiation-emitting substrate; and
growing a nanowire waveguide on the surface of the radiation-emitting substrate using a vapour-liquid-solid mechanism in which the nanoparticle acts as a catalyst to produce an apparatus comprising a nanowire waveguide with first and second ends, the first end attached to the radiation-emitting substrate, the second end comprising the nanoparticle, the nanowire waveguide configured to transmit radiation from the first end to the second end to illuminate the nanoparticle, the apparatus configured such that the nanoparticle is capable of being in close proximity to the analyte to allow for detection of said analyte. The providing of the nanoparticle on the surface of the radiation-emitting substrate may comprise depositing a layer comprising material from which the nanoparticle is to be obtained on the surface of the radiation-emitting substrate and subsequently annealing the radiation-emitting substrate to provide the discrete nanoparticle.

On the other hand, the providing of the nanoparticle on the surface of the radiation-emitting substrate may comprise depositing a layer comprising material from which an array of nanoparticles are to be obtained on the surface of the radiation-emitting substrate and annealing the radiation-emitting substrate to provide an array of nanoparticles. The layer may be patterned to control the locations of the arrays on the surface of the radiation-emitting substrate. The thickness of the layer may be selected to control the size of the nanoparticle.

Electrical contacts may be provided to enable a flow of charge carriers between the radiation-emitting substrate and the nanowire waveguide. First and second electrical contacts may be provided after growing the nanowire waveguide. The first electrical contact may be positioned in physical contact with the radiation-emitting substrate and the second electrical contact may be positioned in physical contact with the nanowire waveguide, such that the first and second electrical contacts are physically isolated from one another. The second electrical contact may be physically isolated from the radiation-emitting substrate and analyte by using electrically insulating material.

According to a further aspect, there is provided an apparatus comprising a means for guiding radiation at a nanoscale with first and second ends, the second end comprising a means for attenuating radiation, the means for guiding radiation at a nanoscale configured to transmit radiation from the first end to the second end to illuminate the means for attenuating radiation, the apparatus configured such that the means for attenuating radiation is capable of being in close proximity to an analyte to allow for detection of said analyte.

According to a further aspect, there is provided a computer program for sensing the presence of an analyte, the computer program comprising computer code to detect the attenuation of radiation by a nanoparticle based on radiation which is transmitted by an apparatus, the apparatus comprising a nanowire waveguide with first and second ends, the second end comprising the nanoparticle, the nanowire waveguide configured to transmit radiation from the first end to the second end to illuminate the nanoparticle, the apparatus configured such that when the nanoparticle is in close proximity to the analyte, it causes attenuation of the radiation.

According to a further aspect, there is provided a computer program for producing an apparatus to allow for detection of an analyte, the computer program comprising computer code to control the growth of a nanowire waveguide on the surface of a radiation emitting substrate using a vapour-liquid-solid mechanism in which a nanoparticle acts as a catalyst to produce an apparatus comprising a nanowire waveguide with first and second ends, the first end attached to the radiation-emitting substrate, the second end comprising the nanoparticle, the nanowire waveguide configured to transmit radiation from the first end to the second end to illuminate the nanoparticle, the apparatus configured such that the nanoparticle is capable of being in close proximity to the analyte to allow for detection of said analyte.

The present disclosure includes one or more corresponding aspects, embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

The excitation of surface plasmons by electromagnetic radiation is known as a surface plasmon resonance (SPR). This phenomenon forms the basis of many standard tools for measuring adsorption of material onto metallic surfaces, and is behind a variety of biological sensor applications.

Figure 1:
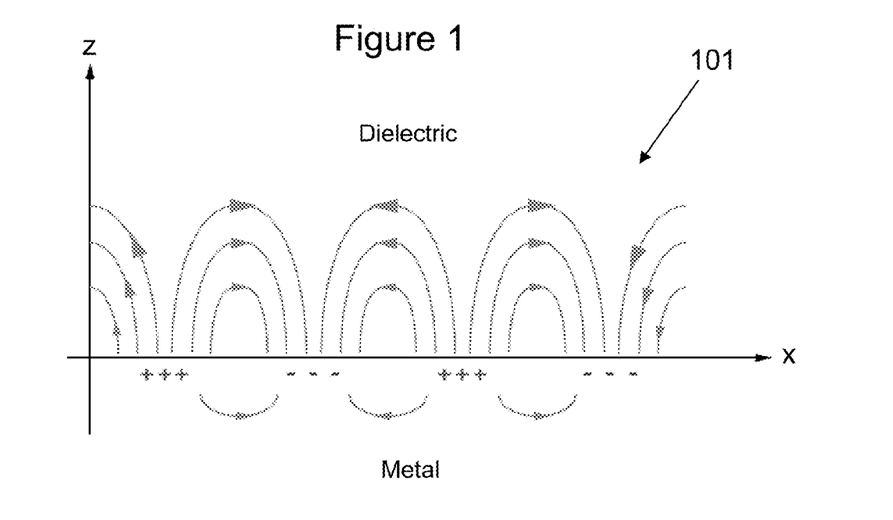
FIG. 1 illustrates schematically a surface plasmon polariton.
Figure 2:
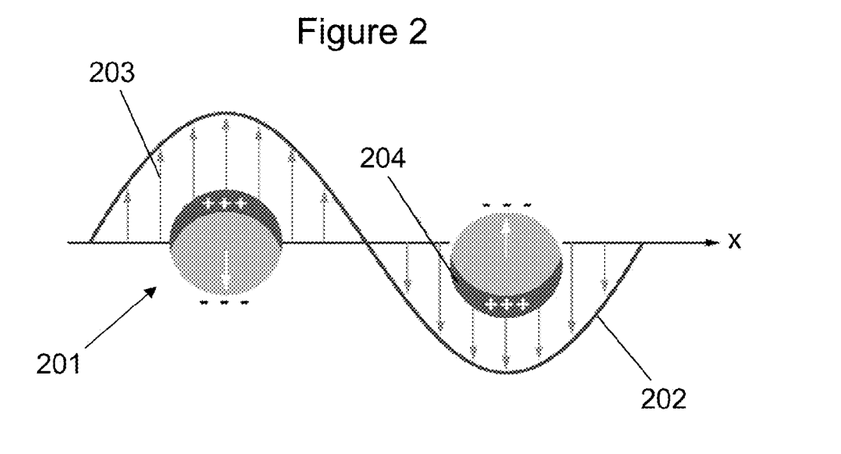
FIG. 2 illustrates schematically a localised surface plasmon.

Surface plasmons (SPs) 101 are surface electromagnetic waves that propagate in a direction parallel to a metal/dielectric interface (FIG. 1). Localised surface plasmons (LSPs), on the other hand, are change density oscillations confined to metallic nanoparticles and metallic nanostructures. FIG. 2 illustrates a plasmon oscillation on the surface of a metal sphere 201 in response to the electric field 203 of an incident electromagnetic wave 202. The displacement of the conduction electron charge cloud 204 is shown.

Excitation of LSPs by electromagnetic radiation results in strong light scattering, the appearance of intense SP absorption bands, and an enhancement of the local electromagnetic fields. A localised surface plasmon resonance (LSPR) is generated when the wavelength of the incident light on the nanoparticle is in resonance with an eigenmode of the nanoparticle plasmon oscillation. The generation of an LSPR is independent of the direction of the incident light. This is a big advantage over SPR systems where special techniques are required in order to achieve the wave vector matching conditions for the excitation of the SPR. LSPR spectroscopy also possesses greater spatial resolution (both lateral and normal to the metal-dielectric interface) than SPR spectroscopy. From Mie scattering theory, the resonance condition for the extinction cross-section for an incident plane wave on a spherical particle is satisfied when, $$\Re[\in_{metal}(\lambda)] + \chi \in_{diel} = 0 \quad \text{(Equation 1)}$$

where $\in_{metal}$ and $\in_{diel}$ are the dielectric constants of the metal and dielectric material, respectively, and $\chi$ is a factor which is dependent on the geometry of the nanoparticle. The value of $\chi$ is 2 for a sphere, but may be as large as 20 for particle geometries with high aspect ratios. Based on this equation, materials which possess a negative real and small positive imaginary dielectric constant are capable of supporting SPs (such as silver and gold). Conditions for excitation are only satisfied, however, if the real dielectric constant of the metal is greater in magnitude than the real dielectric constant of the dielectric material.

The extinction spectrum (absorption plus scattering) of a metal sphere is given as:

$$E(\lambda) = \frac{24\pi^2 Na^3 \varepsilon_{out}^{3/2}}{\lambda \ln(10)} \left[ \frac{\varepsilon_i(\lambda)}{(\varepsilon_r(\lambda) + \chi \varepsilon_{out})^2} \right] \quad \text{(Equation 2)}$$

where $\in_{in}$ and $\in_{out}$ are the dielectric constants of the metal nanoparticle and external environment, respectively, $\in_r$ and $\in_i$ are the real and imaginary components of the wavelength-dependent metal dielectric function, respectively, Na is Avagadro's constant, and $\lambda$ is the wavelength of the incident radiation. The extinction of light associated with the nanoparticle is dependent on any changes in $\in_{out}$ (or refractive index, n, since both are related by $\in = n^2$).

Equations 1 and 2 show that the extinction spectrum (and it is also true for the scattering spectrum) is dependent on the local dielectric environment ($\in_{diel}$ and $\in_{out}$ in equations 1 and 2, respectively). Therefore, any changes in the local environment (dielectric medium surrounding the nanoparticle), such as the presence of an adsorbed species on the surface of the nanoparticle (or simply the dissolution/presence of a species in the surrounding dielectric medium), will cause a shift in the LSPR extinction wavelength maximum (resonance wavelength), $\lambda_{max}$, and a change in intensity. This can be used to detect the type and concentration of adsorbed species.

To affect the LSPR of the nanoparticle, the analyte needs to be located within the evanescent field of the LSPR (i.e. the electromagnetic fields associated with the LSPR). The spatial extent of this local field varies with the wavelength, the complex dielectric constant of the nanoparticle, the nanoparticle size and shape, and the thickness and dielectric constant of any coating on the surface of the nanoparticle. Of course, these parameters are not mutually independent, since the resonance wavelength depends on the size, shape and composition of the nanoparticle and coating. Typically, for metal nanoparticles with resonances in the visible region of the spectrum, the distance between the analyte and the nanoparticle must be of the order of the nanoparticle dimensions before the analyte can be detected. Therefore, the analyte should be held, or should pass, within roughly a diameter of the nanoparticle. Since the evanescent field falls off in an exponential fashion, the closer the analyte is to the nanoparticle, the better the chances of analyte detection using LSPR spectroscopy.

Figure 3:
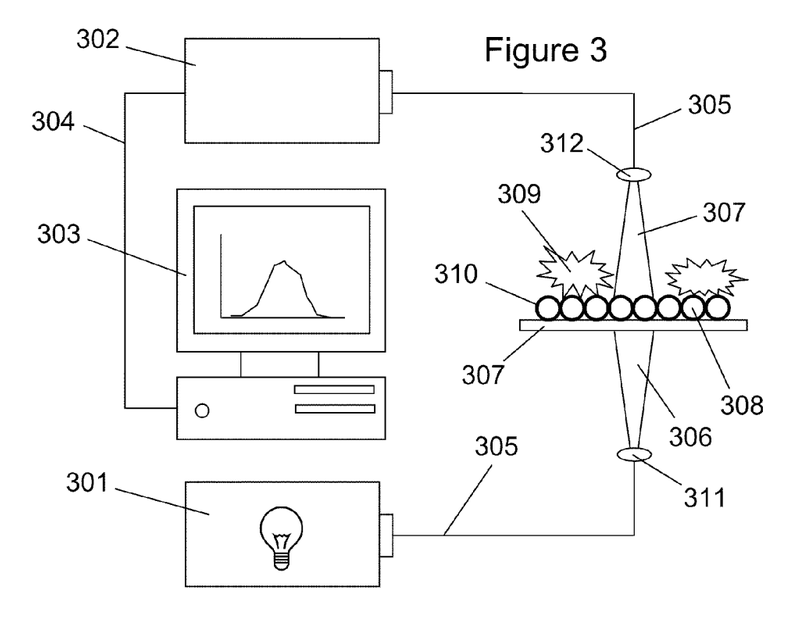
FIG. 3 illustrates schematically a typical LSPR experimental setup for measuring extinction spectra of nanoparticle arrays.

FIG. 3 shows the most straightforward approach to the measurement of nanoparticle LSPR spectra—transmission ultraviolet-visible spectroscopy. Here, one measures the extinction spectrum of the nanoparticles by recording the wavelength dependence of light passing through the sample. In this figure, light 306 from a source 301 is directed along an optical fibre 305 and focused by a lens 311 onto the specimen. The specimen comprises a layer of nanoparticles 308 supported on a transparent substrate 307 which are bound to analyte molecules 309. Although not shown, the specimen is immersed in a dielectric medium, such as air, water or another solvent. The LSPR wavelength will vary depending on the specific dielectric medium. To facilitate binding, the nanoparticles are functionalised with receptor molecules 310. When an LSPR is excited, the wavelengths of light causing the excitation are absorbed and/or scattered. The beam of illumination is detected behind the specimen using the probe 312 of a UV-visible spectrophotometer 302. Light incident on the probe is then directed to a charge-coupled device (CCD) camera (not shown) inside the spectrophotometer. The data is subsequently sent (via electrical cables 304 for example) to a computer 303 for processing, and an extinction spectrum is displayed for analysis.

Figure 4:
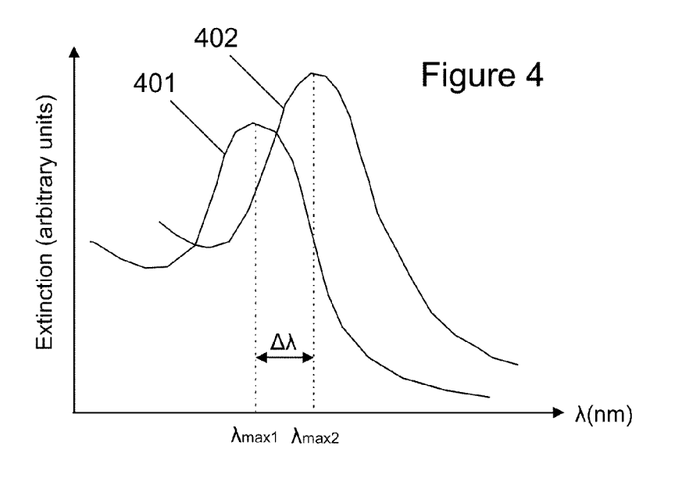
FIG. 4 illustrates schematically a typical LSPR extinction spectrum.

An example of a typical LSPR extinction spectrum is given in FIG. 4, which reveals the absorption and/or scattering of each wavelength of light. The transmission geometry yields the LSPR wavelength as a maximum value in the extinction curve. The peaks from before and after the analytes are bound to the nanoparticles are denoted by numerals 401 and 402, respectively, and the corresponding LSPR wavelengths as $\lambda_{max1}$ and $\lambda_{max2}$. In this case, binding at the surface of the nanoparticles has resulted in a shift in peak wavelength, $\Delta\lambda$, as well as an increase in intensity.

As mentioned in the background section, the necessity for external light sources inhibits miniaturisation and mobility of the sensor, and demands precise alignment of the illumination. There will now be described an LSPR excitation apparatus that may or may not overcome one or more of these issues. A possible method for fabricating such apparatus will also be described.

Figure 5:
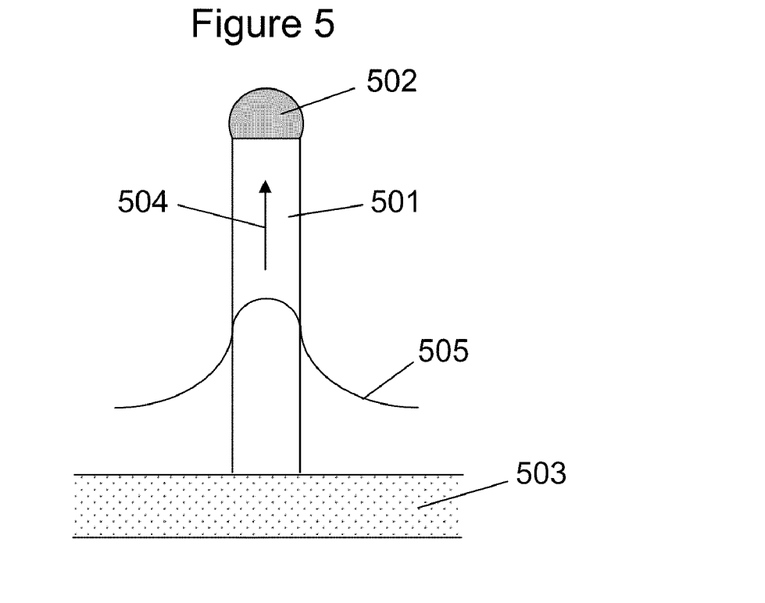
FIG. 5 illustrates schematically a nanowire waveguide on a radiation-emitting substrate.

The apparatus, as illustrated in FIG. 5, comprises an integrated light source and nanowire waveguide 501 which acts to focus and direct the generated light 504 to a nanoparticle 502 attached to the free end of the nanowire waveguide for LSPR excitation and sensing. Integration of the light source and nanowire waveguide may be achieved by forming a p-n junction at the surface of a substrate 503, the nanowire waveguide comprising one side of the junction and the substrate comprising the other side of the junction. One possibility, but by no means the only possible implementation, would be to grow ZnO nanowires epitaxially on a GaN-coated sapphire substrate. If a GaN thin film is doped with Mg, for example, it becomes p-doped. ZnO nanowires are intrinsically n-type due to oxygen vacancies and zinc interstitials within the crystal. Since ZnO and GaN have very little lattice mismatch, ZnO nanowires can be grown in their preferred (0001) growth direction perpendicular to the GaN film. As a result, no further modification is required in order to form the p-n junction.

Figure 6:
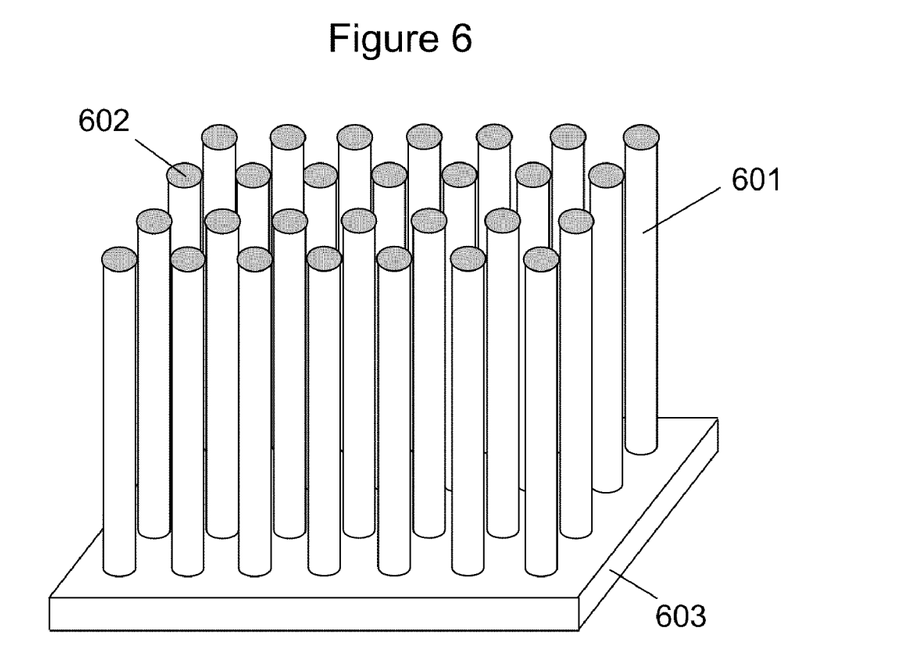
FIG. 6 illustrates schematically an array of nanowire waveguides on a radiation-emitting substrate.
Figure 7:
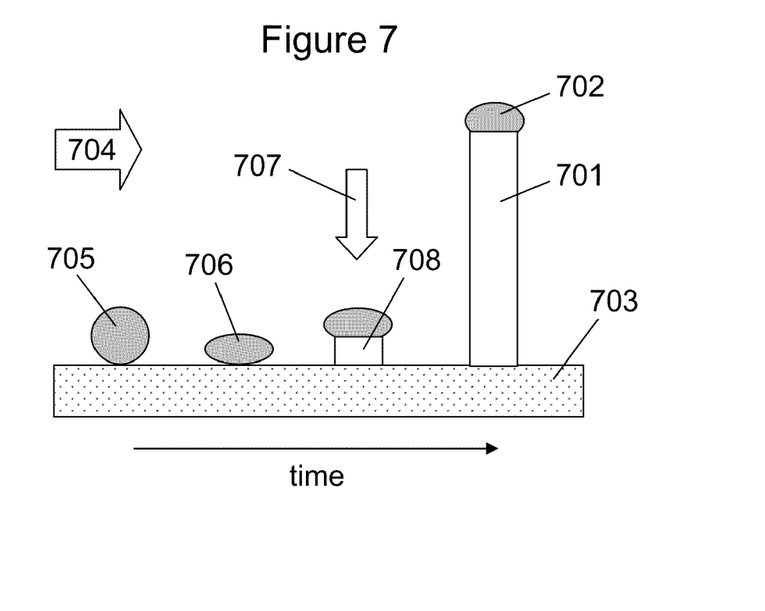
FIG. 7 illustrates schematically the vapour-liquid-solid mechanism used to fabricate the nanowire waveguides.
Figure 11:
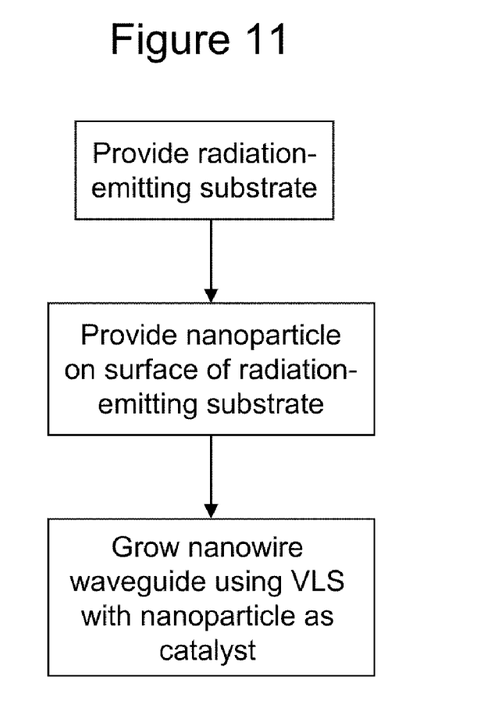
FIG. 11 illustrates schematically a method for fabricating the nanowire waveguides.

Arrays (FIG. 6) of single-crystalline ZnO nanowires can be grown via a vapour-liquid-solid mechanism (VLS) in a vacuum deposition system using gold nanoparticles as catalysts. Growth of a crystal by direct adsorption of a gas onto a solid surface is generally very slow. The VLS method circumvents this by introducing a catalytic liquid alloy phase which can rapidly adsorb a vapour to saturation levels, and from which crystal growth can subsequently occur from nucleated seeds at the liquid-solid interface. The physical characteristics of nanowires grown in this manner depend, in a controllable way, upon the size and physical properties of the liquid alloy. With reference to FIG. 7, a thin layer (or particles 705) of gold is deposited onto the surface of the GaN substrate 703, typically by sputter deposition or thermal evaporation. The substrate is then annealed to create self-assembled liquid gold droplets 706. Lithography can be used to controllably manipulate the diameter and position of the droplets. Following this, Zn and O2 are introduced to the system 704, which react to form a ZnO vapour 707. The Au droplets on the surface of the substrate act to lower the activation energy of normal vapour-solid growth, and absorb ZnO from the vapour state until reaching saturation. Since ZnO has a higher melting point than the ZnO—Au alloy, ZnO precipitates out of the saturated alloy droplet at the liquid-alloy/solid GaN interface in the form of a pillar-like structure 708. As the precipitation of ZnO continues, the height of the pillar increases, resulting in the formation of a ZnO nanowire 701. The Au droplet (nanoparticle 702) used to catalyse the process remains at the free end of the nanowire. This method of synthesis (shown as a flow chart in FIG. 11) is advantageous in that it can produce the integrated light source, nanowire waveguide and nanoparticle sensing tip in a single step without the requirement of further lithographic processing.

The dimensions of the nanowires 601 can be controlled to some degree, with diameters in the range of 50-300 nm and lengths in the range of 1-10 μm. The dimensions of the nanowires are important for this type of device. When the dimensions are less than the wavelength of the guided light the classical "ray" theory is no longer applicable. The fractional mode power within the core of a cylindrical waveguide of radius, r, refractive index, η, with light of wavelength, λ, is given by, $$\eta = 1 - \left[2.405\exp\left(-\frac{1}{V}\right)\right]^2 V^{-3} \qquad \text{(Equation 3)}$$

where the waveguide volume $V=kr(n^2-1)^{1/2}$ and the wavenumber $k=2\pi/\lambda$. For diameters of less than 100 nm, optical confinement is reduced due to diffraction effects. With ZnO nanowires and blue/UV illumination, over 90% of the light is confined within the nanowire waveguide when the diameter is greater than 200 nm. In contrast, less than 25% of the light is confined when the diameter is reduced to 100 nm. For the apparatus described herein, a high degree of optical confinement is preferable, which necessitates the use of nanowires with diameters greater than 100 nm in certain embodiments. Numeral 505 in FIG. 5 illustrates the electromagnetic power profile associated with the guided light within the nanowire.

By appropriate patterning of the catalyst material prior to growth, multiple arrays of nanowires can be grown on the substrate 603. The location of each array on the surface of the substrate may be controlled. By sufficiently spacing the nanowire arrays apart from one another, a single substrate may be used for multiple sensing/detection experiments. As before, each of the as-grown ZnO nanowires are capped at the tip by a gold nanoparticle 602 as a result of the VLS process.

In order to generate light from the p-n junction, electrical contacts need to be added to the structure. Current flows when the p-type material is biased positive with respect to the n-type material causing electrons to recombine with holes at the junction of the device. When the electrons move from the conduction band to the valence band, the difference in energy between the states is emitted as a photon. The photon energy is characteristic of the bandgap of the material. Trap states and defect states give rise to other electron-hole transitions of lower energies and thus generate photons with higher wavelengths.

Figure 8:
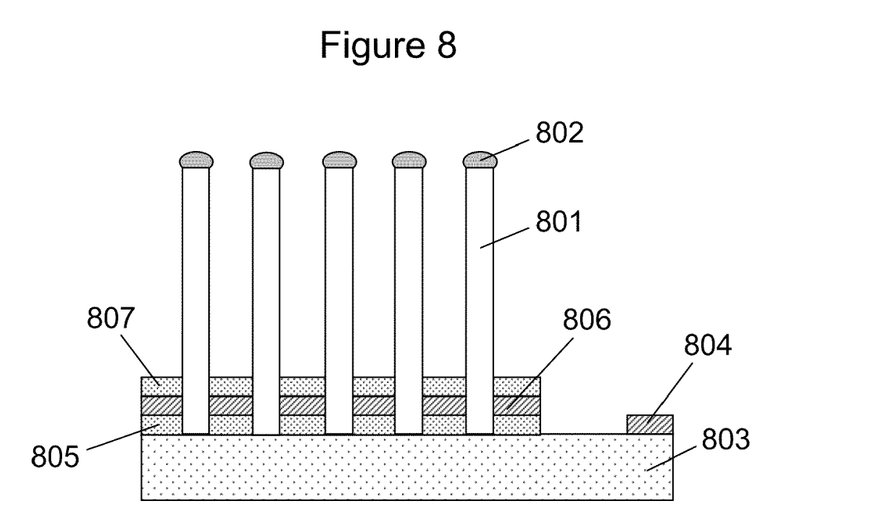
FIG. 8 illustrates schematically the multi-layer structure of the electrical contacts.

Electrical contact may be made to the ZnO nanowires 801 and GaN thin film 803 separately in order to direct the charge carriers across the ZnO—GaN interface. As shown in FIG. 8, an ohmic contact 804 (e.g. Ti/Au) can be deposited directly onto the GaN film. The ZnO nanowire contact, however, is somewhat more complicated. One common method of attaching electrical contacts to nanowire arrays is to deposit (usually by evaporation or sputter deposition) a conducting material on top of the array. For densely packed arrays, this produces a continuous, but porous, film across the tips of the nanowires. For less densely packed arrays, a different approach is to fill the space between the nanowires with insulating material before etching away the surface of the insulating material to expose the tips. Following this, a layer of conducting material is deposited on top of the insulator.

In the present case, however, neither of these methods are applicable because the functioning of the device requires that the nanoparticles 802 at the free ends of the nanowires are not modified. This ensures that LSPRs generated at the metal-dielectric interface are dependent purely on changes in the local dielectric environment.

One approach for the fabrication of the ZnO contact is to make use of a multilayer structure. First, an insulating dielectric layer 805 (such as poly(methyl methacrylate), polystyrene or parylene) is deposited (for example, by spin-casting or evaporation) to prevent direct physical contact between the conductive layer (see below) and the GaN film. If this dielectric layer is not deposited, the charge carriers will follow the path of least resistance and may bypass the nanowire junction altogether. Second, a conductive layer 806 (such as poly(3,4-ethylenedioxythiophene) poly(styrenesulfonate)) is deposited (again by spin-casting or evaporation) to provide the electrical contact. Third, an insulating passivation layer 807 is deposited to prevent direct physical contact between the conductive layer and the local dielectric environment. This layer precludes any chance of the conductive layer affecting the LSPR. The presence of the passivation layer should not affect the LSPR of the nanoparticles as long as it is sufficiently distant, say more than 100 nm from the nanoparticles. To prevent the deposited material (used to form the dielectric, conductive and passivation layers) from modifying the nanoparticles at the tips of the nanowires, plasma etching may be required after each layer is deposited. This should be performed so as to remove the deposited material from the nanoparticles without adversely affecting the multilayer structure. Given the nanowire/substrate geometry and the method of spin-casting, the thickness of the material deposited on the nanoparticles will be less than the thickness of the material deposited on the substrate. In addition, the plasma etch rate at the nanoparticles will be enhanced due to their exposed nature. Both of these factors allow the material deposited on the nanoparticles to be removed without affecting the multilayer structure adversely.

In addition, the dielectric, conductive and passivation layers should be transparent to the light generated at the p-n junction to enable propagation of the illumination along the lengths of the nanowires, and their refractive indices should be as low as possible to promote total internal reflection within the nanowires. These requirements ensure that the intensity of the light incident on the nanoparticles is maximised.

For applications involving the sensing of biomolecular species, specificity of the sensor is incorporated by functionalising the nanoparticle with receptor molecules. The receptor molecules attach to specific functional groups on the analyte, thereby allowing the analyte to bind to the nanoparticle. For example, antibodies are commonly used as the receptor ligand in SPR immunosensors as they specifically attach to their associated antigen. In order that the sensor can be reused, either so that sensing measurements can be repeated or that different analytes can be adsorbed, it is necessary to remove any previously bound receptor molecules from the nanoparticle surface. Here, the electrical connection to the nanowire can be exploited to induce electrodesorption of the receptor molecules. Electrodesorption may be achieved by applying an electrostatic potential to the nanowires to break the metal-receptor bonds. After desorption, the receptor, with or without the attached analyte, can diffuse away from the surface and be removed from the system. The applied potential required to induce desorption must be larger than the potential required to generate light at the p-n junction, otherwise the receptor and analyte will desorb before the nanoparticle is illuminated. A typical desorption potential for n-alkanethiolates is −1.0V with respect to the reference electrode, which is readily achievable with the present system.

Figure 9:
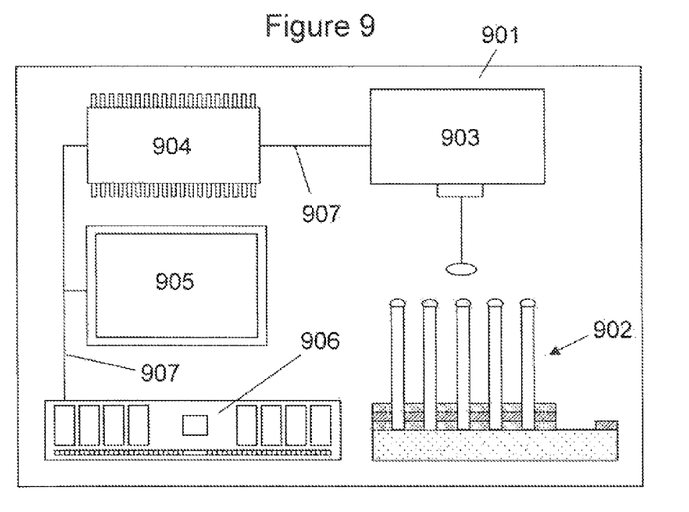
FIG. 9 illustrates schematically a device comprising the apparatus described herein.

FIG. 9 illustrates schematically a sensor device 901 comprising the apparatus 902 described herein. The device further comprises a radiation detector 903, a processor 904, a display apparatus 905 and a storage medium 906, which may be electrically connected to one another by a data bus 907. The function of each device component is best described with respect to FIG. 10, which shows the device is use during a sensing experiment.

Figure 10:
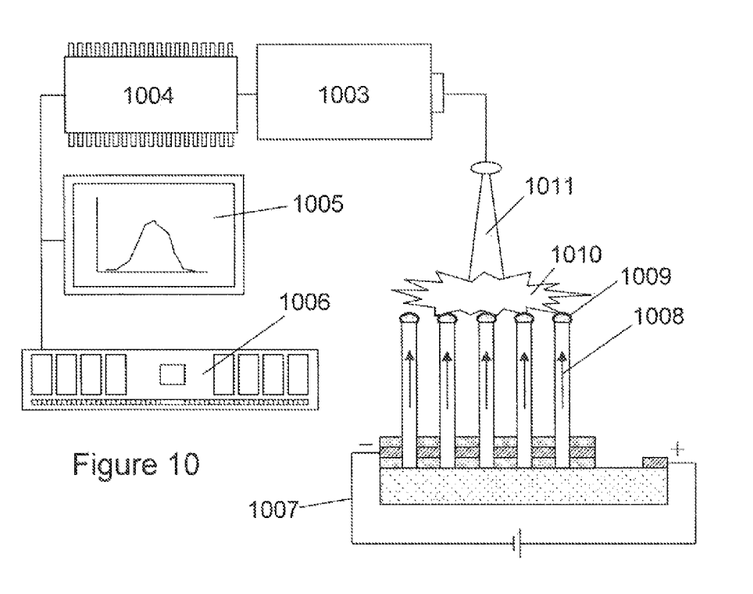
FIG. 10 illustrates schematically the device of FIG. 9 in operation.

After functionalizing the nanoparticles, the analyte 1010 is introduced into the system and adsorbed onto the surface of the nanoparticle tips via the receptor molecules 1009. An electrostatic potential 1007 is then applied across the p-n junction to generate light 1008, which is directed along the length of the nanowire waveguides by total internal reflection. After interacting with the nanoparticles, the light 1011 is detected by the radiation detector 1003 and the signal is passed to the processor 1004. The radiation detector may comprise a CCD camera for converting the optical brightness into an electrical amplitude signal. The processor receives the amplitude signal and processes it for display on the display apparatus 1005. The processor may also perform calculations to identify and quantify the analyte species. The processor may identify and quantify the analyte species by comparing the received data with data previously stored in a database to determine a match. On the other hand, the processor may simply pass the processed data to the display apparatus for manual analysis. The storage medium 1006 is used to store the spectral data, and may also be used to store the database. The storage medium may be a temporary storage medium such as a volatile random access memory, or may be a permanent storage medium such as a hard disk drive, a flash memory or a non-volatile random access memory.

Use of the device 901 will require exchange of the analyte to and from the point of measurement, namely the nanoparticle. For analytes suspended in a common dielectric solvent such as water, this exchange could be controlled using a microfluidic system (not shown).

Microfluidics is the science of designing, manufacturing and formulating devices and processes that deal with the behaviour, precise control and manipulation of fluids that have volumes on a sub-millilitre scale (microlitres, nanolitres or possibly even picolitres). The devices themselves have dimensions ranging from millimetres down to micrometers. The behaviour of fluids at this scale can differ from macrofluidic behaviour in that factors such as surface tension, energy dissipation and fluid resistance start to dominate the system. Microfluidic systems include a number of components (such as pumps, valves, seals and channels etc) specifically adapted to control such small volumes of fluid. Microfluidic systems have diverse and widespread potential applications. In particular, microfluidic biochips utilise microfluidic systems to integrate assay operations such as detection, as well as sample pre-treatment and sample preparation on a single chip.

There are various ways in which the microfluidic system could be incorporated into the present device 901. One approach would be to leave the nanowire field in situ on a larger silicon wafer and then cast a mask out of a polymer such as PDMS to guide the flow to the measurement chamber surrounding the nanowires and provide a mechanism for removing waste from the point of measurement.

A second approach would be to embed the electronic device containing the nanowires within a microfluidic system. This increases the range of materials that can be used when compared to the mask approach. However, it must be emphasized that the best approach is a compromise between the optimal design for the sensing action of the nanowires and the fluidic control required to manipulate the dielectric fluid/analyte.

Figure 12:
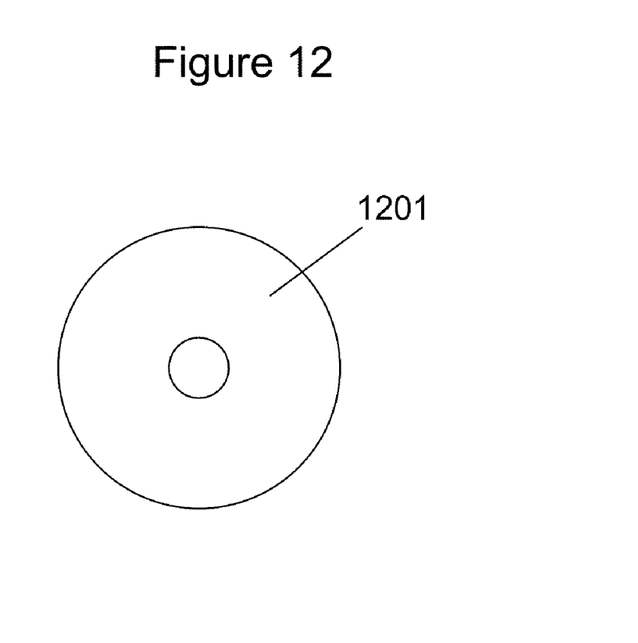
FIG. 12 illustrates schematically a computer readable media providing a first program.
Figure 13:
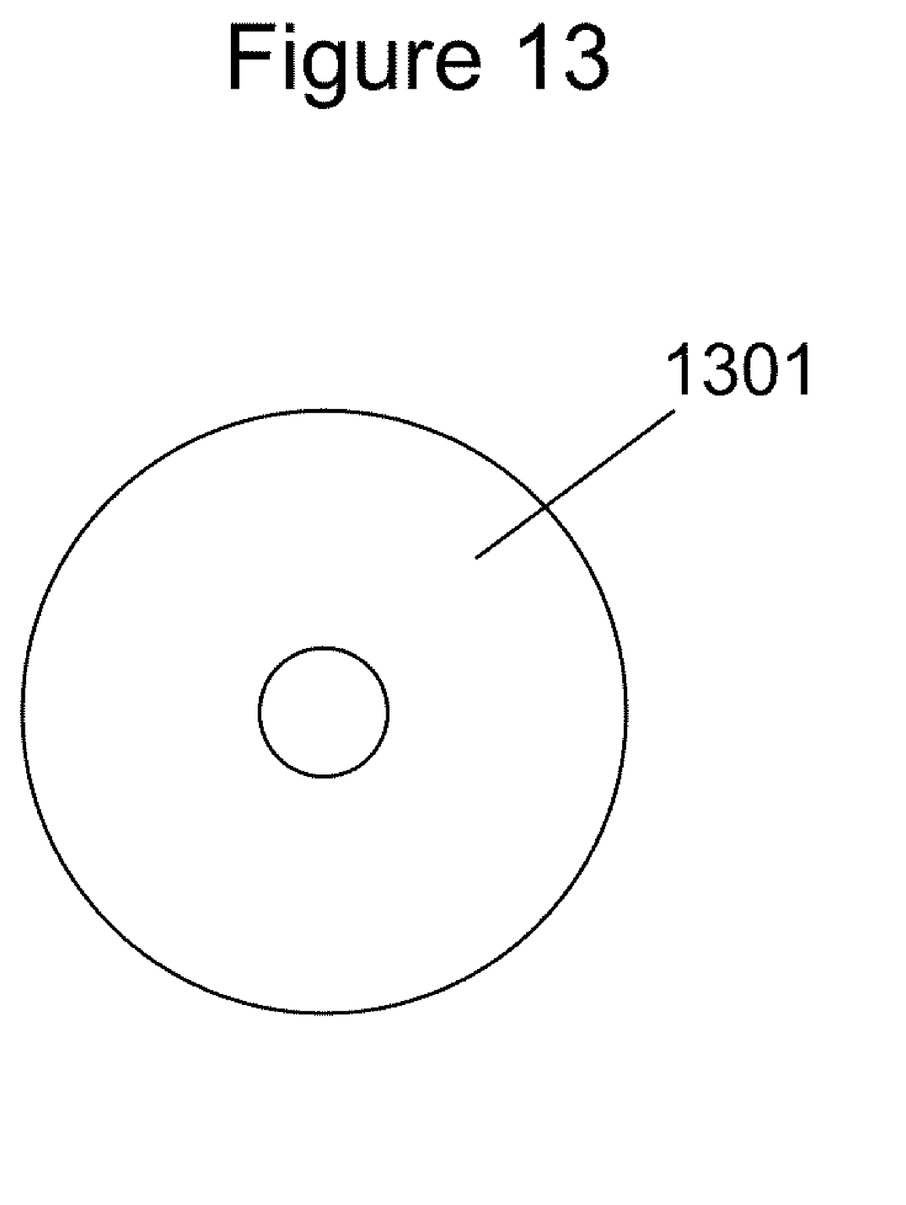
FIG. 13 illustrated schematically a computer readable media providing a second program.

FIGS. 12 and 13 illustrate schematically computer/processor readable media 1201, 1301, each providing a computer program according to one embodiment. The computer program of FIG. 12 may comprise code for sensing the presence of an analyte. The computer program of FIG. 13 may comprise code for producing an apparatus to allow for detection of an analyte. In these examples, the computer/processor readable media are discs such as digital versatile discs (DVDs) or compact discs (CDs). In other embodiments, the computer readable media may be any media that has been programmed in such a way as to carry out an inventive function. The computer readable media may be removable memory devices such as memory sticks or memory cards (SD, mini SD or micro SD).

The computer program of FIG. 12 may comprise code to detect the attenuation of radiation by a nanoparticle based on radiation which is transmitted by an apparatus, the apparatus comprising a nanowire waveguide with first and second ends, the second end comprising the nanoparticle, the nanowire waveguide configured to transmit radiation from the first end to the second end to illuminate the nanoparticle, the apparatus configured such that when the nanoparticle is in close proximity to the analyte, it causes attenuation of the radiation.

The computer program of FIG. 13 may comprise code to control the growth of a nanowire waveguide on the surface of a radiation emitting substrate using a vapour-liquid-solid mechanism in which a nanoparticle acts as a catalyst to produce an apparatus comprising a nanowire waveguide with first and second ends, the first end attached to the radiation-emitting substrate, the second end comprising the nanoparticle, the nanowire waveguide configured to transmit radiation from the first end to the second end to illuminate the nanoparticle, the apparatus configured such that the nanoparticle is capable of being in close proximity to the analyte to allow for detection of said analyte.

Whilst the above description is based around LSPR sensors, the apparatus may utilise other optical transduction phenomena. For example, by placing an emissive species in close proximity to the nanoparticle, the radiation guided by the nanowire could be used to pump (optically excite) the emissive species. The shift in wavelength (or frequency) of the radiation as a result of this excitation can then be detected and used to determine the identity and quantity of the emissive species. Specific examples of emissive species that could be used with the present apparatus include fluorescent, Raman active, or infrared species. Furthermore, half of a fluorescence resonance energy transfer (FRET) pair could also be used.

In the case of a Raman active species, a spectrometer with sufficient resolution to discriminate the Raman shift would be required.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising a nanowire waveguide with first and second ends, the second end comprising a nanoparticle, the nanowire waveguide configured to transmit radiation from the first end to the second end to illuminate the nanoparticle, the apparatus configured such that the nanoparticle is capable of being in close proximity to an analyte to allow for detection of said analyte, wherein:
   the apparatus further comprises a radiation source capable of emitting radiation, the first end of the nanowire waveguide attached to the radiation source to direct radiation generated by the radiation source to the second end of the nanowire waveguide,
   the radiation source is a substrate capable of emitting radiation, and
   the nanoparticle is configured to support surface plasmons, and the radiation emitted by the substrate is configured to excite a localised surface plasmon resonance at the interface between the nanoparticle and the analyte, and wherein the substrate and nanowire waveguide together form a p-n junction of a light-emitting diode.

2. The apparatus of claim 1, wherein the nanoparticle is configured to bind to an analyte to allow for detection of said analyte.

3. The apparatus of claim 1, wherein the substrate comprises a light-emitting diode.

4. The apparatus of claim 1, wherein the apparatus comprises electrical contacts configured to enable a flow of charge carriers between the substrate and the nanowire waveguide.

5. The apparatus of claim 4, wherein the electrical contacts are configured to be physically isolated from the nanoparticle.

6. The apparatus of claim 1, wherein the apparatus comprises first and second electrical contacts, the first electrical contact configured to be in physical contact with the substrate and the second electrical contact configured to be in physical contact with the nanowire waveguide, and wherein the first and second electrical contacts are configured to be physically isolated from one another.

7. The apparatus of claim 6, wherein the second electrical contact is configured to be physically isolated from the substrate and analyte by electrically insulating material.

8. The apparatus of claim 7, wherein the first electrical contact, the second electrical contact, and the insulating material are configured to be transparent to the radiation generated by the substrate.

9. The apparatus of claim 7, wherein the refractive index of the first electrical contact, the second electrical contact, and the insulating material are configured such that total internal reflection of the radiation occurs within the nanowire waveguide.

10. The apparatus of claim 2, wherein the nanoparticle is configured to be functionalised such that it is capable of binding to the analyte.

11. The apparatus of claim 10, wherein the nanoparticle is functionalised by the adsorption of a functionalisation molecule onto the surface of the nanoparticle.

12. The apparatus of claim 11, wherein the apparatus comprises electrical contacts configured to induce electrodesorption of the functionalised molecule at the surface of the nanoparticle.

13. The apparatus of claim 1, wherein the apparatus is configured for use as a transmitter in spectroscopy.

14. The apparatus of claim 1, wherein the apparatus is a module configured for use in a transmitter in spectroscopy.

15. A sensor comprising a radiation detector and the apparatus of claim 1.

16. The sensor of claim 15, wherein the sensor is configured for use in localized surface plasmon resonance spectroscopy.

17. A method for producing an apparatus to allow for detection of an analyte, the method comprising:
providing a radiation-emitting substrate;
providing a nanoparticle on the surface of the radiation-emitting substrate; and
growing a nanowire waveguide on the surface of the radiation emitting substrate using a vapour-liquid-solid mechanism in which the nanoparticle acts as a catalyst to produce an apparatus comprising a nanowire waveguide with first and second ends, the first end attached to the radiation-emitting substrate, the second end comprising a nanoparticle, the nanowire waveguide configured to transmit radiation from the first end to the second end to illuminate the nanoparticle, the apparatus configured such that the nanoparticle is capable of being in close proximity to the analyte to allow for detection of said analyte.

18. An apparatus comprising a means for guiding radiation at a nanoscale with first and second ends, the second end comprising a means for attenuating radiation, the means for guiding radiation at a nanoscale configured to transmit radiation from the first end to the second end to illuminate the means for attenuating radiation, the apparatus configured such that the means for attenuating radiation is capable of being in close proximity to an analyte to allow for detection of said analyte, wherein:
the first end of the means for guiding radiation is attached to a radiation source comprising a substrate capable of emitting the radiation, and
the means for attenuating radiation comprises a nanoparticle configured to support surface plasmons, the radiation emitted by the substrate being configured to excite a localised surface plasmon resonance at the interface between the nanoparticle and the analyte, and wherein the substrate and the means for guiding radiation together form a p-n junction of a light-emitting diode.

19. A computer program for sensing the presence of an analyte, the computer program comprising computer code to detect the attenuation of radiation by a nanoparticle based on radiation which is transmitted by an apparatus, the apparatus comprising a nanowire waveguide with first and second ends, the second end comprising the nanoparticle, the nanowire waveguide configured to transmit radiation from the first end to the second end to illuminate the nanoparticle, the apparatus configured such that when the nanoparticle is in close proximity to the analyte, it causes attenuation of the radiation.

20. A computer program for producing an apparatus to allow for detection of an analyte, the computer program comprising computer code to control the growth of a nanowire waveguide on the surface of a radiation emitting substrate using a vapourliquid-solid mechanism in which a nanoparticle acts as a catalyst to produce an apparatus comprising a nanowire waveguide with first and second ends, the first end attached to the radiation-emitting substrate, the second end comprising the nanoparticle, the nanowire waveguide configured to transmit radiation from the first end to the second end to illuminate the nanoparticle, the apparatus configured such that the nanoparticle is capable of being in close proximity to the analyte to allow for detection of said analyte.

21. The use of an apparatus to allow for detection of an analyte, the use comprising:
providing an apparatus, the apparatus comprising a nanowire waveguide with first and second ends, the second end comprising a nanoparticle, the nanowire waveguide configured to transmit radiation from the first end to the second end to illuminate the nanoparticle, the apparatus configured such that the nanoparticle is capable of being in close proximity to an analyte to allow for detection of said analyte; and
instructing exposure of the apparatus to the analyte to allow for detection of the analyte.

* * * * *